United States Patent
Ma et al.

(10) Patent No.: US 12,380,732 B1
(45) Date of Patent: Aug. 5, 2025

(54) AUXILIARY DIAGNOSIS METHOD AND SYSTEM FOR PARKINSON'S DISEASE BASED ON STATIC AND DYNAMIC FEATURES OF FACIAL EXPRESSIONS

(71) Applicant: Shandong University, Jinan (CN)

(72) Inventors: Xin Ma, Jinan (CN); Xiaochen Huang, Jinan (CN); Yibin Li, Jinan (CN)

(73) Assignee: Shandong University, Jinan (CN)

( * ) Notice: Subject to any disclaimer, the term of this patent is extended or adjusted under 35 U.S.C. 154(b) by 0 days.

(21) Appl. No.: 19/092,775

(22) Filed: Mar. 27, 2025

(51) Int. Cl.
| | |
|---|---|
| *G06V 40/16* | (2022.01) |
| *A61B 5/00* | (2006.01) |
| *G06T 7/00* | (2017.01) |
| *G06V 10/74* | (2022.01) |
| *G06V 10/82* | (2022.01) |
| *G06V 20/40* | (2022.01) |

(52) U.S. Cl.
CPC .......... *G06V 40/176* (2022.01); *A61B 5/4082* (2013.01); *G06T 7/0014* (2013.01); *G06V 10/761* (2022.01); *G06V 10/82* (2022.01); *G06V 20/46* (2022.01); *G06V 20/49* (2022.01); *G06V 40/171* (2022.01); *G06V 40/172* (2022.01); *G06T 2207/10016* (2013.01); *G06T 2207/30201* (2013.01)

(58) Field of Classification Search
CPC .... G06V 40/176; G06V 10/761; G06V 10/82; G06V 20/46; G06V 20/49; G06V 40/171; G06V 40/172; A61B 5/4082; G06T 7/0014; G06T 2207/10016; G06T 2207/30201
See application file for complete search history.

(56) References Cited

U.S. PATENT DOCUMENTS

| | | | | |
|---|---|---|---|---|
| 10,799,186 | B2 * | 10/2020 | Howard | A61B 5/11 |
| 11,113,813 | B2 * | 9/2021 | Alsan | A61B 5/7267 |
| 2014/0315168 | A1 | 10/2014 | Emotient | |

FOREIGN PATENT DOCUMENTS

| | | |
|---|---|---|
| CN | 111310798 A | 6/2020 |
| CN | 111814615 A | 10/2020 |
| CN | 116052872 A | 5/2023 |

OTHER PUBLICATIONS

Gomez et al., "Exploring facial expressions and action unit domains for Parkinson detection", Feb. 2, 2023. (Year: 2023).*

(Continued)

*Primary Examiner* — Phuoc Tran

(57) ABSTRACT

An auxiliary diagnosis method for Parkinson's disease (PD) based on static and dynamic features of facial expressions is provided. Video data of various facial expressions performed by a to-be-tested patient is acquired and pre-processed to extract a plurality of optimal facial expression images corresponding to the various facial expressions. A similarity discrimination is performed on a synthesized happy facial expression image of the to-be-tested patient in a healthy state and an extracted happy facial expression image to obtain similarity features. Distances between multiple facial key points in the various facial expression images are calculated to obtain multiple key features, which are spliced with the plurality of key features to form static features. Coordinate change degrees of multiple facial key points of eyelids and mouth are calculated to obtain dynamic features. A classification prediction result of PD is output based on the spliced features.

4 Claims, 3 Drawing Sheets

(56) References Cited

OTHER PUBLICATIONS

Jin et al., "Diagnosing Parkinson Disease Through Facial Expression Recognition: Video Analysis," 2020. (Year: 2020).*

Luis F. Gomez et al., "Improving Parkinson Detection using Dynamic Features from Evoked Expressions in Video", 2021 IEEE/CVF Conference on Computer Vision and Pattern Recognition Workshops, Sep. 1, 2021, Abstract on p. 1562; last paragraph of Section 1.2, first paragraph of section 2 on p. 1563; second paragraph of left column section 2.1 and 2.2 on p. 1564; section 3.2 on p. 1567.

Changjiang Hu, "Research on the Diagnosis of Parkinson's Disease Based on Facial Expression Images", Chinese Master's Theses Full-text Database Medicine and Health Sciences, No. 3, Mar. 15, 2023, Abstract, Sections 1.4-1.5 on pp. 7-8, Figure 3.2 on p. 23, and section 4.2.3 on p. 39.

Haoyu Tian et al., "Cross-Spatiotemporal Graph Convolution Networks for Skeleton-Based Parkinsonian Gait MDS- UPDRS Score Estimation", IEEE Transactions on Neural Systems and Rehabilitation Engineering, vol. 32, Jan. 10, 2024, pp. 412-421.

* cited by examiner

AUXILIARY DIAGNOSIS METHOD AND SYSTEM FOR PARKINSON'S DISEASE BASED ON STATIC AND DYNAMIC FEATURES OF FACIAL EXPRESSIONS

CROSS-REFERENCE TO RELATED APPLICATIONS

This application claims the benefit of priority from Chinese Patent Application No. 202410367143.X, filed on Mar. 28, 2024. The content of the aforementioned application, including any intervening amendments thereto, is incorporated herein by reference in its entirety.

TECHNICAL FIELD

This application relates to image processing, and more specifically to an auxiliary diagnosis method and system for Parkinson's disease based on static and dynamic features of facial expressions.

BACKGROUND

Parkinson's Disease (PD) is the second most common neurodegenerative disease, mainly affecting the motor control areas of the central nervous system. This disease brings great difficulties to the daily life of patients, as these patients will experience a series of motor and non-motor symptoms. A prominent symptom of PD is facial stiffness. In mild cases, it shows a reduction in facial expressions, and in severe cases, it can lead to the complete loss of facial expressions. This symptom is also known as "Hypomimia".

Traditional diagnosis of PD usually uses assessment scales, such as the non-motor symptoms questionnaire (NMSQuest), the non-motor symptoms scale (NMSS), and the Unified Parkinson's Disease Rating Scale (UPDRS) to comprehensively evaluate the patient's condition. Although these scales are convenient, their reliance on the subjective medical ability of doctors leads to inconsistencies in clinical evaluation. In addition, patients may not be in the best physical and mental state during the medical visit, which affects the accuracy and robustness of these scales.

Objective auxiliary diagnosis systems, such as positron emission tomography (PET), electroencephalogram (EEG), and magnetic resonance imaging (MRI), provide additional support for diagnosis. Although these methods are contact-based, they help doctors formulate treatment plans according to the actual situation of patients, whereas they also increase the psychological pressure and economic burden of patients. Non-contact PD detection methods target modalities (such as voice, gait signals, and facial expressions) based on patients' significant clinical symptoms, and assist in diagnosing Parkinson's disease. These methods not only relieve the burden on patients during medical treatment but also have higher accuracy, enabling a preliminary assessment of PD conditions of the patient. Among them, the method based on facial expressions has a special advantage due to the convenient data acquisition, specifically, it only requires ordinary recording equipment to capture clear images or videos of facial expressions, which is also valuable for the detection of early-stage PD, as subtle losses of facial expressions often occur in the early stages.

Currently, deep learning, especially generative adversarial networks (GANs), has been increasingly applied to PD auxiliary diagnosis. There are already studies for PD prediction, where a generative network is used to synthesize normal facial expression images to train a ResNet-based network, and the trained network is used for PD prediction. In addition, other studies have incorporated facial key points and action units (AUs) into PD diagnosis to extract facial key points from images to calculate expression factors. Due to issues such as the insufficiency of PD facial datasets, some methods have also started to use statistical analysis and automatic emotion detection. However, analysis and processing of most of the existing models are based on static facial images. Dynamic characteristics of facial expressions are rarely concerned, or continuous video data/image data are less used for PD auxiliary diagnosis. The accuracy of PD diagnosis based solely on the features of static facial images is still relatively low.

SUMMARY

To address the above-mentioned deficiencies in prior art, the present disclosure provides an auxiliary diagnosis method and system for Parkinson's disease (PD) based on static and dynamic features of facial expressions. By extracting the dynamic and static features from continuous video footage of imitated facial expressions, the degree of expression deficiency and facial stiffness/inflexibility can be comprehensively captured. Then, these two types of features are fused for auxiliary diagnosis of PD, effectively improving the accuracy of PD diagnosis.

Technical solutions of the present disclosure are described below.

In a first aspect, the present disclosure provides an auxiliary diagnosis method for Parkinson's disease (PD) based on static and dynamic features of facial expressions, comprising:

acquiring video data of various facial expressions performed by a to-be-tested patient;

pre-processing the video data to extract a plurality of optimal facial expression images corresponding to the various facial expressions;

synthesizing, using a generative network, a happy facial expression image of the to-be-tested patient in a healthy state to obtain a synthesized happy facial expression image; performing, based on a neutral facial expression image, a similarity discrimination, on the synthesized happy facial expression image and an extracted happy facial expression image to obtain similarity features; calculating distances between multiple facial key points in the various facial expression images to obtain a plurality of key features; splicing the similarity features and the plurality of key features to form static features;

calculating, based on the plurality of optimal facial expression images, coordinate change degrees of multiple facial key points of eyelids and mouth to obtain dynamic features; and equilibrating dimensions of the static features and the dynamic features, followed by feature splicing using a static-dynamic feature balanced classification network to obtain spliced features; and outputting a classification prediction result of PD based on the spliced features.

In a second aspect, this application provides an auxiliary diagnosis system for PD based on static and dynamic features of facial expressions, comprising:

a data acquisition module;

a data pro-processing module;

a static feature extraction module;

a dynamic feature extraction module; and a classification prediction module;

wherein the data acquisition module is configured to acquire video data of various facial expressions performed by a to-be-tested patient;

the data pro-processing module is configured to pre-process the video data to extract a plurality of optimal facial expression images corresponding to the various facial expressions;

the static feature extraction module is configured to synthesize a happy facial expression image of the to-be-tested patient in a healthy state using a generative network to obtain a synthesized happy facial expression image and perform a similarity discrimination on the synthesized happy facial expression image and an extracted happy facial expression image based on a neutral facial expression image to obtain similarity features; calculate distances between multiple facial key points in the various facial expression images to obtain a plurality of key features; and splice the similarity features and the plurality of key features to form static features;

the dynamic feature extraction module is configured to calculate coordinate change degrees of multiple facial key points of eyelids and mouth to obtain dynamic features based on the plurality of optimal facial expression images; and the classification prediction module is configured to balance dimensions of the static features and the dynamic features, followed by feature splicing using a static-dynamic feature balanced classification network to obtain spliced features; and output a classification prediction result of PD based on the spliced features In a third aspect, this application provides an electronic device, comprising:

a memory; and a processor;

wherein the memory is configured to store computer instructions; and the processor is configured to execute the computer instructions to implement the aforementioned auxiliary diagnosis method.

In a fourth aspect, this application provides a computer-readable storage medium, wherein the computer-readable storage medium is configured to store computer instructions; and the computer instructions are configured to be executed by a processor to implement the aforementioned auxiliary diagnosis method.

The beneficial effects of the present disclosure are described below.

(1) The present disclosure provides an auxiliary diagnosis method and system for Parkinson's disease based on static and dynamic facial expression features. By extracting dynamic features and static features from continuous simulated facial expression videos, the method comprehensively captures the degree of facial expression deficiency and facial rigidity/stiffness. Through fusion of the dynamic features and the static features for PD auxiliary diagnosis, the accuracy of PD diagnosis is effectively improved.

(2) In the present disclosure, a generative network and facial key point analysis on static images of simulated expressions of Parkinson's patients are utilized to construct static facial features, thereby quantifying and characterizing the degree of facial expression deficiency. Motion features of key facial regions are extracted from continuous videos of facial expressions of Parkinson's patients, and are configured as dynamic features, thereby quantifying and characterizing the degree of facial rigidity. A static-dynamic feature balanced classification network is employed to address the data discrepancy between static and dynamic features, thereby enhancing the accuracy of PD classification prediction. Compared to existing non-contact PD diagnosis methods, the method provided in the present disclosure achieves superior prediction accuracy (94%) and recall rate (98%) through comprehensive analysis of static facial expression features and dynamic facial expression features.

BRIEF DESCRIPTION OF THE DRAWINGS

The illustrative drawings forming part of the present disclosure are intended to provide a further understanding of the present disclosure. The exemplary embodiments and descriptions herein are intended to explain the present disclosure, rather than constituting undue limitations thereon.

DETAILED DESCRIPTION OF EMBODIMENTS

Figure 1:
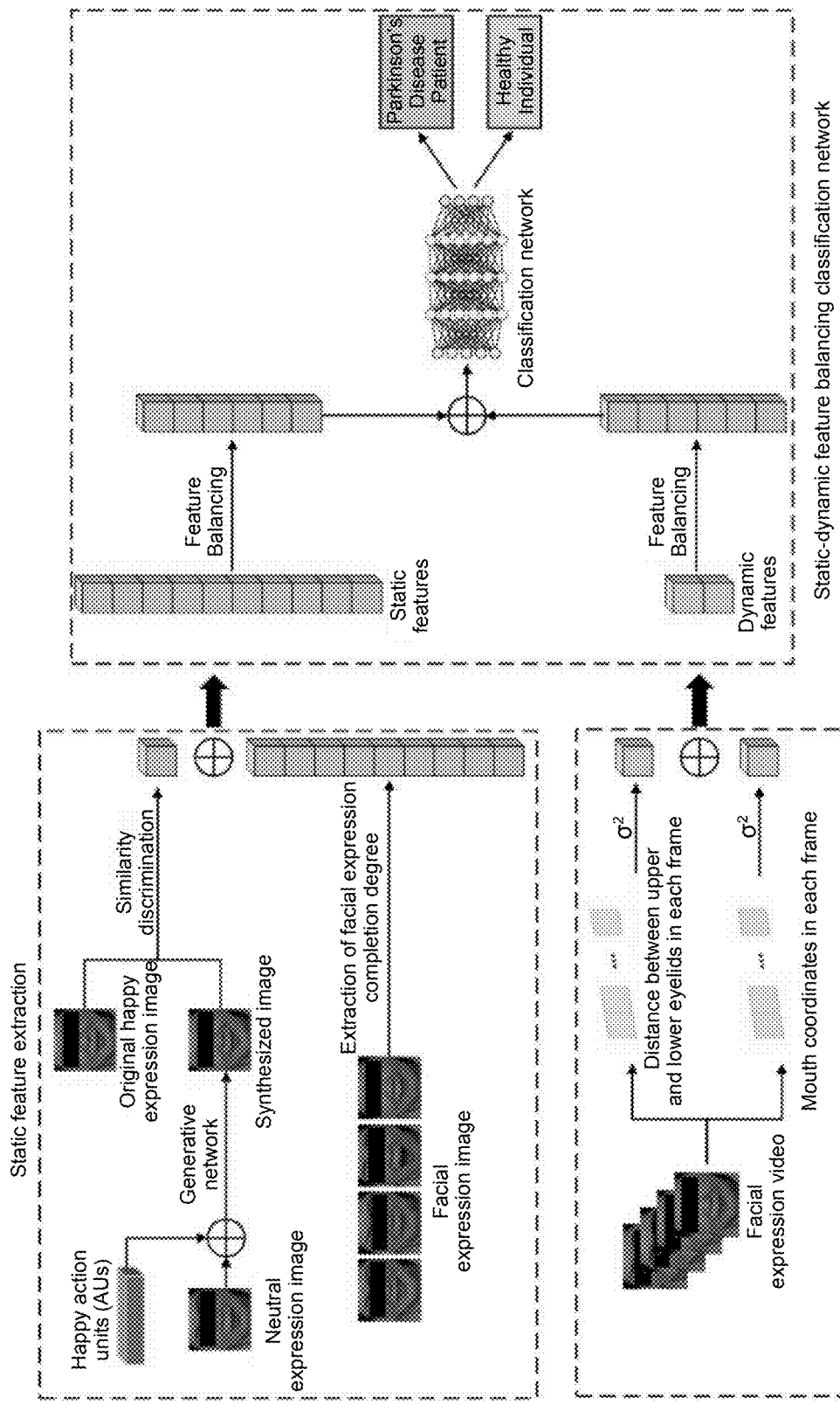
FIG. 1 illustrates a structural diagram of a classification prediction model according to an embodiment of the present disclosure.

It should be noted that the detailed description provided below is exemplary and is intended merely to illustrate specific embodiments of the present disclosure, thereby providing further explanation of the present disclosure, rather than limiting the present disclosure to the exemplary embodiments described. Unless otherwise specified, all technical and scientific terms used herein have the same meaning as commonly understood by those of ordinary skill in the prior art. Furthermore, it should be understood that as used herein, the terms, such as "comprising" and/or "including", indicate the presence of features, steps, operations, devices, components, and/or combinations thereof.

Embodiment 1

Parkinson's disease (PD), as a common neurodegenerative disorder, presents complex symptoms that are challenging to diagnose directly and accurately. To address this issue, the present embodiment provides an auxiliary diagnosis method for PD based on static and dynamic facial expression features. By analyzing facial expressions, the method detects the primary symptom of facial expression deficiency in Parkinson's patients. The method primarily includes the following critical steps. Firstly, a complex generative network is utilized to generate synthetic images of a patient exhibiting basic emotions (e.g., "happiness") under healthy conditions. These synthetic images are compared with the patients' actual facial expressions to extract completion degrees of facial expressions from other emotional images of the patient, thereby constructing static features for assessing facial expression deficiency. Secondly, facial movements of the patient in an expression video are analyzed to construct dynamic features that quantify degree of facial muscle rigidity. Finally, a specialized static-dynamic feature balanced classification network is used to integrate the extracted static and dynamic features to complete the auxiliary diagnosis and discrimination of PD. This method effectively enables more convenient and accurate PD auxiliary diagnosis for patients.

An auxiliary diagnosis method for PD based on static and dynamic features of facial expressions includes the following steps.

Video data of various facial expressions performed by a to-be-tested patient are acquired.

The video data are pre-processed to extract a plurality of optimal facial expression images corresponding to the various facial expressions.

A happy facial expression image of the to-be-tested patient in a healthy state is synthesized using a generative network to obtain a synthesized happy facial expression image. Based on a neutral facial expression image, a similarity discrimination is performed on the synthesized happy facial expression image and an extracted happy facial expression image to obtain similarity features. Distances between multiple facial key points in the various facial expression images are calculated to obtain a plurality of key features. The similarity features and the plurality of key features are spliced to form static features.

Based on the plurality of optimal facial expression images, coordinate change degrees of multiple facial key points of eyelids and mouth are calculated to obtain dynamic features.

Dimensions of the static features and the dynamic features are balanced, followed by feature splicing using a static-dynamic feature balanced classification network to obtain spliced features. A classification prediction result of PD is output based on the spliced features.

The auxiliary diagnosis method for PD based on static and dynamic features of facial expressions is further described below.

(S1) Video data of various facial expressions performed by a to-be-tested patient are acquired.

During video data acquisition, the to-be-tested patient sits in front of a screen displaying images of seven basic facial expressions (i.e., neutral, happiness, sadness, surprise, fear, anger, and disgust). Each expression is presented in three separate images sourced from the publicly available Oulu_CASIA dataset. The images are sequentially displayed to the to-be-tested patient, who mimics the shown expressions. This process is recorded by a camera, with auxiliary lighting provided to ensure adequate illumination on the face of the to-be-tested subject, thereby guaranteeing stable and high-quality video capture.

(S2) The video data are pre-processed to extract a plurality of optimal facial expression images corresponding to the various facial expressions.

The complete video data obtained from step (S1) includes seven basic facial expressions. During data processing, the entire video is divided into seven segments, i.e., seven individual videos, each individual video corresponding to a distinct facial expression.

For each individual video representing a specific facial expression, the optimal facial state of this expression is captured to acquire the optimal facial expression image. This process encounters several challenges, which are addressed through data preprocessing.

Issue 1: Facial tremor of the patient during recording.

Facial key points can be categorized into relatively fixed points and dynamic flexible points. The relatively fixed points are baseline points, while the dynamic flexible points help in measuring the displacement of baseline points. For example, points around the nose are considered the relatively fixed points. To mitigate minor facial tremors during recording, the following steps are applied to consecutive video-frame images in each individual video. Facial key points (as marked in FIG. 2) in each video-frame image and annotated. Coordinates of each facial key point are converted into relative coordinates based on the relatively fixed points to normalize all video-frame images using. The normalization formula for facial key points is expressed as:

$$x_{center}=(x_{28}+x_{29}+x_{30}+x_{31}+x_{34})/5;$$

$$y_{center}=(y_{28}+y_{29}+y_{30}+y_{31}+y_{34})/5;$$

$$x'_i=|x_i-x_{center}|; \text{ and}$$

$$y'_i=|y_i-y_{center}|;$$

where $x_i$ and $y_i$ represent horizontal and vertical coordinates of the $i^{th}$ facial key point, respectively; $x_{28}$, $y_{28}$, $x_{29}$, $y_{29}$, $x_{30}$, $y_{30}$, $x_{31}$, $y_{31}$, $x_{34}$ and $y_{34}$ correspond to coordinates of facial key points labeled 28, 29, 30, 31, and 34, which are located around the nose; and $x_i'$ and $y_i'$ denote the transformed coordinates of the $i^{th}$ facial key point after normalization.

Through the above coordinate transformation, the issue of facial tremor during recording is effectively resolved.

Issue 2: Variations in distance between the patient and camera due to movements of the patient toward or away from the camera during recording.

K images are uniformly selected from a neutral-expression independent video of the patient. An average value of coordinates of each facial key point in the K images is calculated to obtain key point coordinates of an average neutral face (ANF). This mitigates inconsistencies caused by changes in distance between the patient and camera, thereby solving the issue 2.

Issue 3: The patient cannot maintain optimal facial states consistently throughout the expression video.

To extract frames that best represent the target facial expression state, for video-frame images in each expression-specific independent video, a distance between each facial key point in each video-frame image and a key point in the average neutral face corresponding thereto is calculated. Video-frame images of each expression-specific independent video are sorted in a descending order according to a sum of distances of all key points in each video-frame image to screen the first L images (in this embodiment, L=5) as the optimal facial expression state images. As such, the issue 3 is solved.

Through the above preprocessing steps, 35 facial expression images are obtained for each patient. Finally, facial alignment is performed using OpenFace, and the facial expression images are cut into 128×128 pixels.

(S3) Feature extraction.

In this embodiment, static features and dynamic features are extracted and analyzed from facial expression videos of PD patients to enable PD diagnosis. The entire classification and prediction process is implemented through a classification-prediction model. As illustrated in FIG. 1, a complex generative network is used to synthesize happy facial expression images of the patient. These synthesized images are compared with the happy facial expression images self-imitated by the patient. An expression completion degree is calculated based on the similarity between the imitated expression images and synthesized expression images, which serves as static features. The motion of facial regions in the expression video that may reflect symptoms of facial rigidity is analyzed, and the analyzed results are configured as dynamic features. Here, the static features reflect the completeness of the facial expressions of the patient, while the dynamic features characterize the degree of facial stiffness.

(S3.1) Static feature extraction.

In this embodiment, the static features are extracted from two perspectives. (1) A generative network is used to synthesize a happy facial expression image of the patient in a healthy state, and the training strategy of the generative network is optimized to enhance the quality of synthesized images. Specifically, the neutral expression image of the patient and the action unit sequence images filtered from a dataset to represent the happy expression are input into the generative network to output the synthesized happy facial expression image in the healthy state, and the similarity between the synthesized image and the happy facial expression image of the patient is calculated and used as a part of the static features. (2) The expression completion degree is extracted based on key facial features. Particularly, the expression completion degrees for four basic emotions (happiness, sadness, surprise, anger) are extracted to configure as another part of the static features.

Furthermore, the static feature extraction is performed through analyzing facial expression images of the patient. PD patients often exhibit "unnatural" smiles due to the absence of cheek-raising movements. To address this, the generative network is used to synthesize happy-facial expression images of the patient in a healthy state, which is compared with their actual happy-facial expression image. Expression completion degrees of the imitated expressions (i.e., happiness, sadness, surprise and anger) of the patient are calculated, and the results are configured as the static features of PD patient representing the deficiency in facial expressiveness characteristic.

(S3.1.1) A happy facial expression image of the to-be-tested patient in a healthy state is synthesized using a generative network to obtain a synthesized happy facial expression image. Based on a neutral facial expression image, a similarity discrimination is performed on the synthesized happy facial expression image and an extracted happy facial expression image to obtain similarity features.

A generator model and a discriminator model are trained through adversarial processes to create a high-quality image generator. After extensive testing, GANimation is selected as the generative model in this embodiment. GANimation, based on action unit (AU) annotations, can capture facial movements that define human expressions within a continuous manifold. An important capability of this model is to focus on synthesizing key facial regions while keeping other parts of the image unchanged.

A training dataset for the GANimation network is constructed, including the CelebFacesAttributes (CelebA) dataset and the seeprettyface dataset. To enhance the training set with diverse facial images and improve the robustness of the network under various lighting conditions, the CelebA dataset with diversity, large capacity and abundant annotations, is incorporated. The CelebA dataset is a large-scale facial attribute dataset containing over 200,000 celebrity images, and each annotated with 40 attributes. These images exhibit various poses and backgrounds. Additionally, the seeprettyface dataset is included to improve the performance of the network on different faces. This dataset consists of high-resolution images generated by the StyleGAN network, ensuring no duplicate images in the dataset.

To further enhance the robustness of the generative network, the A-class face dataset from the seeprettyface dataset is added, and A-class faces are regarded as targets for the auxiliary diagnostic method for PD. OpenFace is used to extract the AUs from the facial images.

Finally, the training dataset is used to train the generative network model. For GANimation, the goal is to learn a mapping (M) that can transform a reference image ($I_{yr}$) into an output image ($I_{yg}$) conditioned on the target AU ($y_g$). To synthesize more diverse results, the original network uses random AUs as $y_g$ during training. However, the training strategy is modified in this embodiment to focus on generating happy expression images from neutral images. To this end, a "happy AUs database" is created from 8,000 happy expression images and their extracted AUs. During training, there is a 60% probability of using the previous random AU generation method and a 40% probability of selecting AUs from the "happy AUs database." To prevent overfitting, random noise is introduced when selecting AUs from the "happy AUs database", thereby enhancing the diversity of the network.

The happy facial expression image of the to-be-tested patient under in a healthy state is synthesized using the trained generative network described above. Then, the synthesized happy facial expression image is compared with the actual extracted happy facial expression image to perform similarity discrimination, thereby obtaining similarity features.

Specifically, after image synthesis, image similarity evaluation is conducted. The main methods for extracting facial image features include image descriptors, deep learning-based methods, and facial expression dynamic analysis.

Existing research shows that humans primarily express happiness through changes in the mouth, characterized by raised corners of the mouth and slightly parted lips. Therefore, M synthesized happy images and N images of the happy expression images of the patient are selected. The coordinates of the facial key points around the mouth in these images are extracted and compared. This comparison provides a quantitative measure of the facial expression deficiency of the patient.

The Euclidean distance between two points is defined as:

$$d(p_i, p_j) = \sqrt{(x_i - x_j)^2 + (y_i - y_j)^2};$$

where x and y represent the coordinates of point p.

Euclidean distances between the same facial key points in each synthesized image and each extracted image are calculated to obtain the similarity discrimination result. This similarity discrimination result is defined as:

$$D_1 = \frac{1}{M \times N \times 20} \sum_{i=1}^{M} \sum_{j=1}^{N} \sum_{mouth=49}^{68} d(P_{i,mouth}, P_{j,mouth});$$

where i and j represent coordinates of the synthesized happy facial expression image and the extracted happy facial expression image, respectively; and ($p_{i,mouth}$) and ($p_{j,mouth}$) represent the key points of the mouth, i.e., key points 49 to 68.

The similarity discrimination result obtained from the above calculation is defined as the similarity feature.

(S3.1.2) Distances between multiple facial key points across various facial expression images are calculated to obtain a plurality of key features.

PD can cause cognitive impairment and affect expressive abilities, leading to cortical or peripheral nerve trauma that restricts the production of facial expressions and emotional recognition. To evaluate the completion degree of facial expressions in PD patients, the positional relationships of key facial regions in images of patients mimicking different expressions are analyzed. Through repeated experimental analyses, four representative expressions, i.e., happiness, sadness, surprise and anger, are selected herein to assess expression completion.

For the happy expression, characterized by raised mouth corners and slightly-opened lips, the analysis includes calculating the distance variation between predefined points near the mouth corners (as marked in FIG. 2) and relatively fixed points for the happy expression with raised mouth corners, and measuring the distance change between the upper and lower lips for the happy expression with slightly-opened lips. Notably, these distance changes are relative to the neutral expression image. For example, the distance change refers to the difference in distance between the upper and lower lips between the happy expression image and the neutral expression image.

For the sad expression, characterized by drooping eyebrows and drooping mouth corners, the analysis includes calculating the distance variation between the eyebrows and relatively fixed points, and the distance variation between points near the mouth corners and relatively fixed points, to characterize the sad expression.

For the surprised expression, characterized by increased distance between the eyebrows and eyes, widened eyes, and opened mouth, the analysis includes calculating the distance variation between the eyebrows and the lower part of the eyes, the distance change between the upper and lower eyelids, and the distance change between the upper and lower lips to characterize the surprised expression.

For the angry expression, characterized by furrowed brows (manifested as lowered eyebrows and reduced distance between the eyebrows and eyes), the analysis includes calculating the distance variation between the eyebrows and relatively fixed points for lowered eyebrows, and the distance change between the eyebrows and the center of the eyes for the reduced distance between the eyebrows and eyes.

Figure 2:
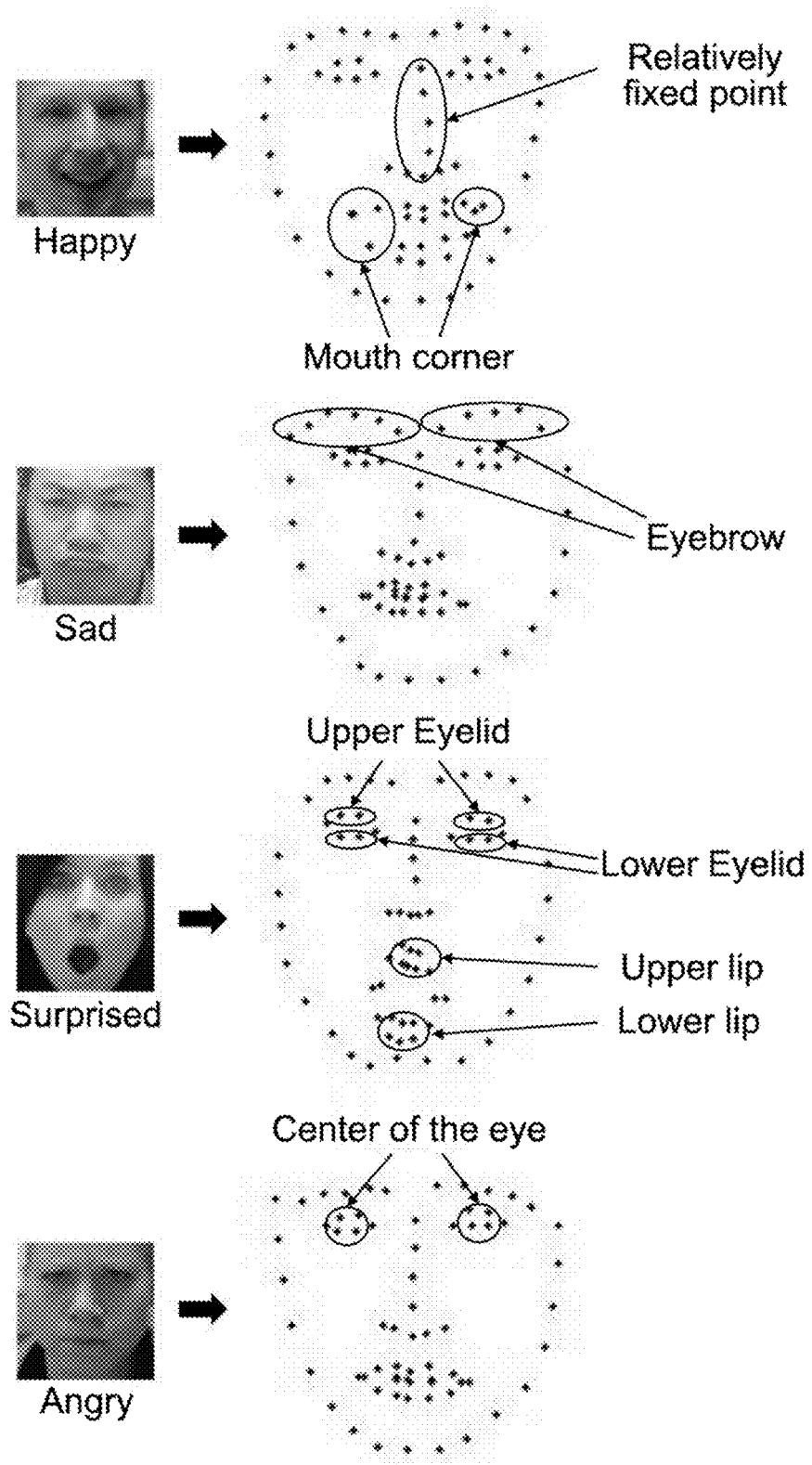
FIG. 2 schematically depicts facial expression images with annotations of different facial regions and facial key points therein according to an embodiment of the present disclosure.

The positions of different facial regions and the key points within these regions are shown in FIG. 2, where the left column displays expression images from the publicly available Oulu-CASIA dataset (as these images are publicly accessible, they do not involve privacy concerns), and the right column shows the corresponding distribution of facial key points. Table 1 below presents the key facial regions used to calculate the completion degree of facial expressions in PD patients. The distances between key points in these key facial regions are used to quantify the degree of facial expression impairment, thereby precisely determining their spatial relationships.

TABLE 1

Facial Features and Corresponding Regions

| Facial Features | Region A | Region B |
| --- | --- | --- |
| Raised mouth corners | Mouth corners | Relatively fixed points |
| Slightly-opened lip | Upper lip | Lower lip |
| Drooping eyebrow | Eyebrow | relatively fixed points |
| Dropping Mouth corners | Mouth corners | relatively fixed points |
| Increased distance between the eyebrows and eyes | Eyebrow | Center of eyes |
| Widened eyes | Upper eyelid | Lower eyelid |
| Opened mouth | Upper lip | Lower lip |
| Drooping eyebrow | Eyebrow | relatively fixed points |
| Reduced distance between the eyebrows and eyes | Eyebrow | Center of eyes |

However, considering that the positions of facial regions vary among individuals, only analyzing the expression images of the patient may compromise the robustness of the algorithm. Therefore, when calculating facial positional relationships, the same calculations are performed on the imitated expression images and neutral expression images of the patient. The differences in the calculation results are treated as static features, which represent the degree of facial expression impairment in PD patients and eliminate inter-individual variations in facial characteristics.

(S3.1.3) The similarity features and the plurality of key features are spliced to form the static features. Through this process, a 9-dimensional vector is generated for each patient, configuring as the static feature vector.

(S3.2) Dynamic Feature Extraction. Faces of PD patients are often described as mask-like face, exhibiting little or no expression. In addition, the facial expressions of the patient also show significant rigidity, particularly noticeable in the reduced frequency of spontaneous blinking. Neurophysiological studies on PD indicate that patients exhibit smaller amplitudes and slower speeds in facial voluntary movements. Therefore, to assess the rigidity of facial expressions in PD patients, dynamic facial features must be extracted, focusing on the movements of the eyes and mouth. In this embodiment, based on multiple facial expression images from the expression videos of the patient, the degree of coordinate variation in multiple facial key points of the eyelids and mouth is calculated using variance, which are configured as the dynamic feature.

(S3.2.1) The coordinates of facial key points are extracted from multiple expression images of various facial expressions. Based on the extracted key point coordinates, the positional relationship between the upper and lower eyelids is calculated, and the degree of coordinate variation in the eye region is determined by using variance. Specifically, although PD affects eye movements of the patients, the correlation between blinking frequency and other PD symptoms is not significant. Therefore, blinking frequency should not be used to quantify facial rigidity. In practice, each patient performs seven basic facial expressions, each requiring changes in the eye region. Experimental results show differences in the amplitude of eye size changes between PD patients and healthy control groups. Thus, for each patient and each expression, facial key point coordinates are extracted from 35 facial images (5 images per expression) of each patient, and the positional relationship between the upper and lower eyelids is calculated. Then, variance analysis is used to determine the degree of variation in the eye region.

For n samples, the variance is defined as:

$$\mathrm{Var}(x) = \frac{\sum_{i=1}^{n}(x_i - \bar{x})^2}{n}.$$

If for n points, the variance is defined as:

$$\mathrm{Var}(p) = \frac{\sum_{i=1}^{n}(x_i - \bar{x})^2}{n} + \frac{\sum_{i=1}^{n}(y_i - \bar{y})^2}{n};$$

where $x_i$ and $y_i$ represent coordinates of the $i^{th}$ point among the n points.

The distance $E_i$ between the upper and lower eyelids in the $i^{th}$ facial image is defined as:

$$E_i = \frac{1}{4}(d(p_{i,38}, p_{i,42}) + d(p_{i,29}, p_{i,41}) + d(p_{i,44}, p_{i,48}) + d(p_{i,45}, p_{i,47}));$$

where $p_{i,n}$ represent key points of the eyelid region in the $i^{th}$ facial image.

The variation in the eye region is defined as:

$$D_{11} = \text{Var}(E);$$

where E represents the distance between the upper and lower eyelids in each facial expression image of the patient.

(S3.2.2) Based on the extracted key point coordinates, the movements of each facial key point in the mouth region are calculated, and the degree of coordinate variation in the mouth region is determined by using variance calculation. Specifically, emotional information is not uniformly distributed across the face. Generally, humans rely more on the mouth than the eyes when discerning facial expressions. When making various expressions, the mouth of the patient needs to undergo corresponding changes. However, due to facial rigidity in PD patients, the amplitude of mouth movements decreases during continuous facial changes. Therefore, in this embodiment, the key point coordinates of the mouth region are extracted, and the movement of each point is calculated. By variance analysis, the amplitude of mouth movements exhibited by the patient during a series of continuous facial expression changes is determined. The calculation formula is expressed by:

$$D_{12} = \sum_{i=49}^{68} \text{Var}(p_i);$$

where $p_i$ represents coordinates of the $i^{th}$ key point in each facial expression image of the patient.

(S3.2.3) Each calculation result is configured as a feature, such that a plurality of dynamic features are obtained. Specifically, to estimate the rigidity of the face of the patient, two results are obtained, i.e., the variation in the eye region and the movement of the mouth region. The two calculation results constitute two dynamic features.

(S4) The dimensions of the static features and dynamic features are balanced followed by feature splicing, and the classification prediction result for PD is output based on the spliced features.

In practice, the weights of the static feature and the dynamic feature should be equal for PD auxiliary diagnosis. However, after feature extraction, the actual number of data points for the static feature and the dynamic feature is not equal. Therefore, to ensure equal weights for static and dynamic features, these features are first input into a feature equilibrating network. This network transforms the two sets of features into six dimensions each, thereby equilibrating the weights between the static feature and the dynamic feature without altering the number of data points. This process ensures that the weights of the static feature and the dynamic feature are equal in the PD diagnostic model. The balanced features are then concatenated, and PD classification is performed to complete the PD auxiliary diagnosis task.

Further, each facial expression video of the patient generates a 12-dimensional vector, where $D_1$-$D_{10}$ represent static features, and $D_{11}$-$D_{12}$ represent dynamic features. The meanings of each data point are shown in Table 2 below. Subsequently, the feature data is input into the designed static-dynamic feature equilibrating classification network for PD classification.

TABLE 2

Meaning of static feature and dynamic feature data

| Data | Meaning |
|---|---|
| D1 | Similarity of synthesized images |
| D2 | Degree of mouth opening in happy expression |
| D3 | Degree of mouth opening in the happy expression |
| D4 | Degree to which the eyebrows are furrowed in the sad expression |
| D5 | The degree to which the corners of the mouth droop in the sad expression |
| D6 | The distance between the eyebrows and the eyes in the surprised expression |
| D7 | How open the mouth is in the surprised expression |
| D8 | How wide the eyes are open in the surprised expression |
| D9 | The degree to which the eyebrows are furrowed in the angry expression |
| D10 | Distance between eyebrows and eyes in an angry expression |
| D11 | The degree of change in mouth movement |
| D12 | Degree of change in eyelid distance |

Figure 3:
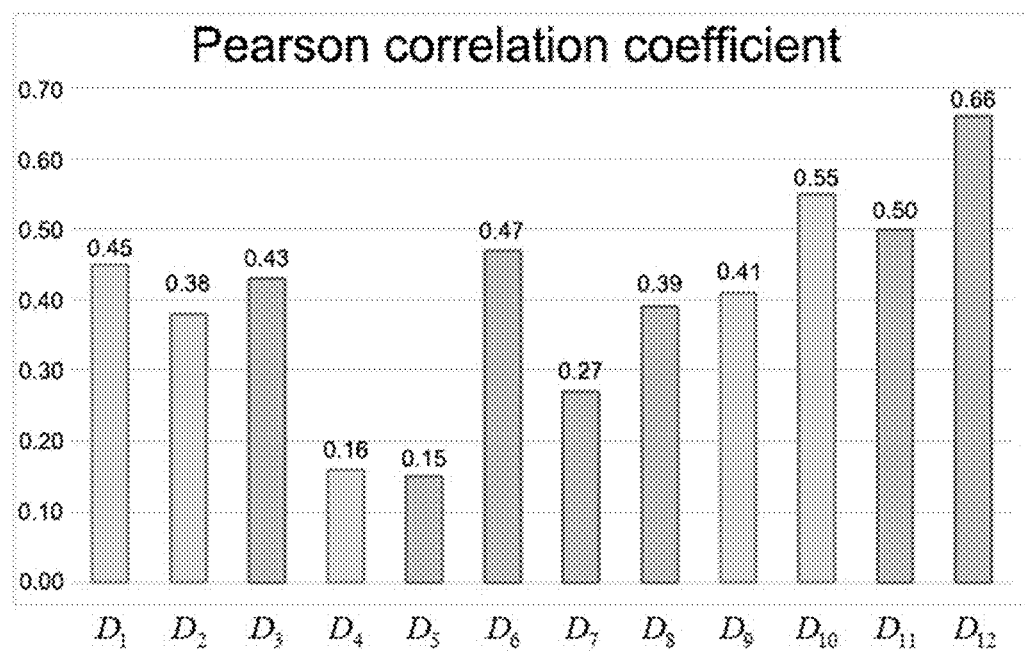
FIG. 3 is a Pearson correlation coefficient pattern among static facial features and dynamic facial features and Parkinson's disease according to an embodiment of the present disclosure.

As an alternative implementation, this embodiment employs generative networks and facial key points to meticulously study the facial expression data of PD patients. Data of each patient is encapsulated in a one-dimensional vector (static-dynamic feature concatenation) composed of 12 data points. Additionally, this embodiment explores the correlation between the data points and PD by calculating the Pearson correlation coefficient. The Pearson correlation coefficient quantifies the strength and direction of the linear relationship between two variables, with an absolute value exceeding 0.2 indicating moderate correlation and exceeding 0.4 indicating strong correlation. The results in FIG. 3 demonstrate that most data points in this embodiment exhibit significant correlations with PD, thereby validating the rationality of the extracted static-dynamic features.

In this embodiment, to address the lack of publicly available datasets for facial expressions of PD, sufficient training data is collected to construct a PD facial expression video (PDFEV) dataset, which is used to train the aforementioned classification prediction model. Specifically, the dataset includes videos from 62 PD patients (25 males and 37 females, with an average age of 62.8 years±7.6 years). Additionally, it also includes 23 healthy control subjects (11 males and 12 females, with an average age of 58.6 years±6.1 years). Each subject is recorded performing seven basic facial expressions, i.e., neutral expression, happy expression, sad expression, surprised expression, fearful expression, angry expression, and disgusted expression. The method described in step (S1) is employed for data collection, with verbal instructions provided on how to perform each expression, considering the typically weaker facial expressiveness of PD patients. Furthermore, to protect patient privacy, the eye regions are removed from both the original and synthesized facial expression images of PD patients.

Furthermore, based on the aforementioned dataset, the feature equilibrating network is trained with reference to a neural network classifier to improve prediction accuracy. In this embodiment, five-fold cross-validation is employed to evaluate the performance of the network, achieving an average accuracy of 94.1%, which demonstrates high classification accuracy and effectively enhances the precision of Parkinson's disease diagnosis.

To further validate the superiority of the method proposed in this embodiment, additional experiments are conducted for verification.

The improved GANimation generative network is trained on the CelebA dataset and the seeprettyface dataset. The training set includes 231,990 images, and the test set includes 25,000 images. The GANimation model is trained with a batch size of 16 over 50 epochs, with each epoch consisting of 14,499 steps. The Adam optimizer is used with exponential decay rates $\eta_1=0.5$ and $\eta_2=0.999$ for moment estimates set. The learning rate begins to decay after the initial 20 epochs. The model is implemented using PyTorch, and all experiments are conducted on a server equipped with a 13$^{th}$ Gen Intel® Core™ i9-13900K CPU and an NVIDIA® GeForce RTX 4090 GPU. The improved GANimation network adopts a tailored training strategy, successfully generating happy expression images of healthy individuals. Additionally, after incorporating the A-class face dataset, the network becomes more stable in generating images with A-class facial features.

For each to-be-test patient, 12 data points are collected to classify PD. In addition to the static-dynamic feature equilibrating classification (SDFEC) network, multiple classification algorithms are employed, including Bayesian Classifier (BC), Random Forest (RF), Decision Tree (DT), Support Vector Machine (SVM), and Deep Neural Network (DNN).

To assess the robustness of the models, five-fold cross-validation is used, and the results are presented in Table 3. The SDFEC in this embodiment demonstrated superior performance in equilibrating the learning of static features and dynamic features, achieving the highest accuracy (94%) and recall rate (98%), making it particularly suitable for the task and resulting in better classification accuracy. Furthermore, the SDFEC also achieves the highest Cohen's Kappa coefficient (0.83), indicating that this method achieves better consistency across the entire dataset. Additionally, Table 3 lists the classification results using only static features or dynamic features, showing that combining static features and dynamic features yields higher accuracy in PD classification than using a single feature alone.

TABLE 3

Performance comparison of different Models using different features for classification

| Model | Feature | Accuracy | Precision | Recall | F1 Score | Cohen's Kappa |
|---|---|---|---|---|---|---|
| BC | SD | 0.73 | 0.85 | 0.77 | 0.8 | 0.38 |
|  | Happiness | 0.78 | 0.84 | 0.88 | 0.85 | 0.41 |
|  | Sadness | 0.75 | 0.77 | 0.9 | 0.84 | 0.22 |
|  | Surprise | 0.82 | 0.85 | 0.9 | 0.88 | 0.49 |
|  | Angry | 0.81 | 0.84 | 0.91 | 0.87 | 0.46 |
|  | SF | 0.88 | 0.95 | 0.88 | 0.91 | 0.71 |
|  | DF | 0.85 | 0.9 | 0.9 | 0.89 | 0.64 |
|  | SF-DF | 0.9 | 0.97 | 0.9 | 0.93 | 0.76 |
| RF | SD | 0.67 | 0.79 | 0.76 | 0.76 | 0.19 |
|  | Happiness | 0.66 | 0.78 | 0.76 | 0.75 | 0.15 |
|  | Sadness | 0.71 | 0.79 | 0.81 | 0.8 | 0.25 |
|  | Surprise | 0.81 | 0.84 | 0.91 | 0.87 | 0.47 |
|  | Angry | 0.81 | 0.86 | 0.88 | 0.87 | 0.51 |
|  | SF | 0.9 | 0.91 | 0.9 | 0.92 | 0.7 |
|  | DF | 0.82 | 0.89 | 0.87 | 0.88 | 0.54 |
|  | SF-DF | 0.9 | 0.91 | 0.96 | 0.93 | 0.73 |
| DT | SD | 0.67 | 0.79 | 0.75 | 0.76 | 0.19 |
|  | Happiness | 0.65 | 0.76 | 0.74 | 0.74 | 0.14 |
|  | Sadness | 0.64 | 0.77 | 0.68 | 0.73 | 0.16 |
|  | Surprise | 0.77 | 0.81 | 0.9 | 0.85 | 0.38 |
|  | Angry | 0.76 | 0.82 | 0.87 | 0.84 | 0.35 |
|  | SF | 0.87 | 0.91 | 0.92 | 0.91 | 0.65 |
|  | DF | 0.75 | 0.86 | 0.8 | 0.82 | 0.39 |
|  | SF-DF | 0.88 | 0.89 | 0.95 | 0.92 | 0.68 |
| SVM | SD | 0.71 | 0.75 | 0.92 | 0.82 | 0.1 |
|  | Happiness | 0.8 | 0.81 | 0.89 | 0.87 | 0.43 |
|  | Sadness | 0.78 | 0.79 | 0.9 | 0.86 | 0.39 |
|  | Surprise | 0.82 | 0.85 | 0.91 | 0.87 | 0.53 |
|  | Angry | 0.75 | 0.79 | 0.88 | 0.83 | 0.32 |
|  | SF | 0.9 | 0.89 | 0.9 | 0.92 | 0.76 |
|  | DF | 0.82 | 0.86 | 0.91 | 0.88 | 0.56 |
|  | SF-DF | 0.9 | 0.78 | 0.97 | 0.93 | 0.73 |
| DNN | SD | 0.72 | 0.8 | 0.81 | 0.82 | 0.24 |
|  | Happiness | 0.68 | 0.8 | 0.78 | 0.77 | 0.19 |
|  | Sadness | 0.71 | 0.82 | 0.79 | 0.77 | 0.29 |
|  | Surprise | 0.83 | 0.89 | 0.88 | 0.88 | 0.57 |
|  | Angry | 0.8 | 0.82 | 0.86 | 0.91 | 0.45 |
|  | SF | 0.89 | 0.92 | 0.92 | 0.93 | 0.72 |
|  | DF | 0.71 | 0.86 | 0.78 | 0.74 | 0.37 |
| SDFEC | SF-DF | 0.92 | 0.93 | 0.95 | 0.97 | 0.78 |
|  | SF-DF | 0.94 | 0.95 | 0.98 | 0.96 | 0.83 |

Embodiment 2

An auxiliary diagnosis system for PD based on static and dynamic features of facial expressions is provided herein, which includes a data acquisition module, a data pre-processing module, a static feature extraction module, a dynamic feature extraction module and a classification prediction module.

The data acquisition module is configured to acquire video data of various facial expressions performed by a to-be-tested patient.

The data pro-processing module is configured to pre-process the video data to extract a plurality of optimal facial expression images corresponding to the various facial expressions.

The static feature extraction module is configured to synthesize a happy facial expression image of the to-be-tested patient in a healthy state using a generative network to obtain a synthesized happy facial expression image and perform a similarity discrimination on the synthesized happy facial expression image and an extracted happy facial expression image based on a neutral facial expression image to obtain similarity features; calculate distances between multiple facial key points in the various facial expression images to obtain a plurality of key features; and splice the similarity features and the plurality of key features to form static features.

The dynamic feature extraction module is configured to calculate coordinate change degrees of multiple facial key points of eyelids and mouth to obtain dynamic features based on the plurality of optimal facial expression images.

The classification prediction module is configured to balance dimensions of the static features and the dynamic features, followed by feature splicing using a static-dynamic feature balanced classification network to obtain spliced features; and output a classification prediction result of PD based on the spliced features.

Embodiment 3

An electronic device is provided herein, which includes a memory and a processor. The memory is configured to store computer instructions. The processor is configured to execute the computer instructions to implement the aforementioned auxiliary diagnosis method.

Embodiment 4

A computer-readable storage medium is provided herein. The computer-readable storage medium is configured to store computer instructions. The computer instructions are configured to be executed by a processor to implement the aforementioned auxiliary diagnosis method.

The steps and methods involved in Embodiments 2-4 above correspond to those in Embodiment 1. For specific implementation details, please refer to the relevant description in Embodiment 1. The term "computer-readable storage medium" should be understood to include a single medium or multiple media containing one or more sets of instructions; it should also be understood to include any medium capable of storing, encoding, or carrying a set of instructions for execution by a processor and enabling the processor to perform any method in the present disclosure.

One of ordinary skill in the art should understand that the modules or steps of the present disclosure described above can be implemented using general-purpose computing devices. Alternatively, they can be implemented using program code executable by computing devices, thereby allowing them to be stored in storage devices for execution by computing devices, or fabricated into individual integrated circuit modules, or combining multiple modules or steps into a single integrated circuit module. The present disclosure is not limited to any specific combination of hardware and software.

Described above are only the preferred embodiments of the present disclosure. Although the specific implementations of the present disclosure have been described with reference to the accompanying drawings, these descriptions do not limit the scope of protection of the present disclosure. It should be understood that, based on the technical solutions of the present disclosure, various modifications or adaptations made without creative effort by one of ordinary skill in the art still fall within the scope of protection of the present disclosure.

What is claimed is:

1. An auxiliary diagnosis method for Parkinson's disease (PD) based on static and dynamic features of facial expressions, comprising:
   acquiring video data of various facial expressions performed by a to-be-tested patient;
   pre-processing the video data to extract a plurality of optimal facial expression images corresponding to the various facial expressions;
   synthesizing, using a generative network, a happy facial expression image of the to-be-tested patient in a healthy state to obtain a synthesized happy facial expression image; performing, based on a neutral facial expression image, a similarity discrimination, on the synthesized happy facial expression image and an extracted happy facial expression image to obtain similarity features; calculating distances between multiple facial key points in the various facial expression images to obtain a plurality of key features; splicing the similarity features and the plurality of key features to form static features;
   calculating, based on the plurality of optimal facial expression images, coordinate change degrees of multiple facial key points of eyelids and mouth to obtain dynamic features; and
   equilibrating dimensions of the static features and the dynamic features, followed by feature splicing using a static-dynamic feature balanced classification network to obtain spliced features; and outputting a classification prediction result of PD based on the spliced features;
   wherein the video data is pre-processed through steps of:
      splitting the video into a plurality of independent videos, each of the plurality of independent videos corresponds to a facial expression;
      annotating facial key points for consecutive video-frame images of each of the plurality of independent videos; convert coordinates of each facial key point to relative coordinates based on a relatively fixed point; and performing normalization processing on the video-frame images;
      uniformly selecting K images from a neutral-expression independent video; and calculating an average value of coordinates of each facial key point in the K images to obtain key point coordinates of an average neutral face; and
      for video-frame images in each expression-specific independent video, calculating a distance between each facial key point in each video-frame image and a key point in the average neutral face corresponding thereto; sorting video-frame images of each expression-specific independent video in a descending order according to a sum of distances of all key points in each video-frame image to screen the first L images as the optimal facial expression state images;
   the various facial expressions comprise a neutral facial expression, a happy facial expression, a sad facial expression, a surprised facial expression, a fearful facial expression, an angry facial expression, and a disgusted facial expression; and the facial key points comprise relatively fixed points and dynamic flexible points, the relatively fixed points comprise points around a nose;

the similarity discrimination is performed through steps of:
  acquiring M synthetic happy facial expression images and N extracted happy facial expression images;
  extracting coordinates of facial key points around a mouth from the acquired images; and
  calculating Euclidean distance between the same facial key point in each synthetic image and each extracted image to obtain similarity discrimination results, and the discrimination results are configured as similarity features;

the plurality of key features are obtained through steps of:
  for a happy facial expression image, calculating distance variations between points near mouth corners and the relatively fixed points, and distance changes between an upper lip and a lower lip;
  for a sad facial expression image, calculating distance variations between eyebrows and the relatively fixed points, and distance variations between points near mouth corners and the relatively fixed points;
  for a surprised facial expression image, calculating distance variations between eyebrows and lower eyelids, distance variations between an upper eyelid and a lower eyelid, and distance variations between an upper lip and a lower lip;
  for an angry facial expression image, calculating distance variations between eyebrows and the relatively fixed points, and distance variations between eyebrows and eye centers; and
  configuring differences between calculation results from synthetic images and extracted images as the plurality of key features;
  wherein all the distance variations are measured relative to a neutral facial expression image; and the dynamic features are obtained through steps of:
  extracting facial key point coordinates from the plurality of facial expression images;
  calculating positional relationships between upper and lower eyelids using extracted facial key point coordinates, and determining variation degrees of eye region key points through variance calculation;
  calculating movement patterns of each key point in a mouth region using extracted facial key point coordinates, and determining variation degrees of the key points in the mouth region through variance calculation; and
  configuring calculation results as the dynamic features.

2. An auxiliary diagnosis system for PD based on static and dynamic features of facial expressions, comprising:
  a data acquisition module;
  a data pro-processing module;
  a static feature extraction module;
  a dynamic feature extraction module; and
  a classification prediction module;
  wherein the data acquisition module is configured to acquire video data of various facial expressions performed by a to-be-tested patient;
  the data pro-processing module is configured to pre-process the video data to extract a plurality of optimal facial expression images corresponding to the various facial expressions;
  the static feature extraction module is configured to synthesize a happy facial expression image of the to-be-tested patient in a healthy state using a generative network to obtain a synthesized happy facial expression image and perform a similarity discrimination on the synthesized happy facial expression image and an extracted happy facial expression image based on a neutral facial expression image to obtain similarity features; and calculate distances between multiple facial key points in the various facial expression images to obtain a plurality of key features; and splice the similarity features and the plurality of key features to form static features;
  the dynamic feature extraction module is configured to calculate coordinate change degrees of multiple facial key points of eyelids and mouth to obtain dynamic features based on the plurality of optimal facial expression images; and
  the classification prediction module is configured to balance dimensions of the static features and the dynamic features, followed by feature splicing using a static-dynamic feature balanced classification network to obtain spliced features; and output a classification prediction result of PD based on the spliced features;
  wherein the video data is pre-processed through steps of:
    splitting the video into a plurality of independent videos, each of the plurality of independent videos corresponds to a facial expression;
    annotating facial key points for consecutive video-frame images of each of the plurality of independent videos; convert coordinates of each facial key point to relative coordinates based on a relatively fixed point; and performing normalization processing on the video-frame images;
    uniformly selecting K images from a neutral-expression independent video; and calculating an average value of coordinates of each facial key point in the K images to obtain key point coordinates of an average neutral face; and
    for video-frame images in each expression-specific independent video, calculating a distance between each facial key point in each video-frame image and a key point in the average neutral face corresponding thereto; sorting video-frame images of each expression-specific independent video in a descending order according to a sum of distances of all key points in each video-frame image to screen the first L images as the optimal facial expression state images;
  the various facial expressions comprise a neutral facial expression, a happy facial expression, a sad facial expression, a surprised facial expression, a fearful facial expression, an angry facial expression, and a disgusted facial expression; and
  the facial key points comprise relatively fixed points and dynamic flexible points, the relatively fixed points comprise points around a nose;
  the similarity discrimination is performed through steps of:
    acquiring M synthetic happy facial expression images and N extracted happy facial expression images;
    extracting coordinates of facial key points around a mouth from the acquired images; and
    calculating Euclidean distance between the same facial key point in each synthetic image and each extracted image to obtain similarity discrimination results, and the discrimination results are configured as similarity features;

the plurality of key features are obtained through steps of:

for a happy facial expression image, calculating distance variations between points near mouth corners and the relatively fixed points, and distance changes between an upper lip and a lower lip;

for a sad facial expression image, calculating distance variations between eyebrows and the relatively fixed points, and distance variations between points near mouth corners and the relatively fixed points;

for a surprised facial expression image, calculating distance variations between eyebrows and lower eyelids, distance variations between an upper eyelid and a lower eyelid, and distance variations between an upper lip and a lower lip;

for an angry facial expression image, calculating distance variations between eyebrows and the relatively fixed points, and distance variations between eyebrows and eye centers; and configuring differences between calculation results from synthetic images and extracted images as the plurality of key features; and wherein all the distance variations are measured relative to a neutral facial expression image;

the dynamic features are obtained through steps of:

extracting facial key point coordinates from the plurality of facial expression images;

calculating positional relationships between upper and lower eyelids using extracted facial key point coordinates, and determining variation degrees of eye region key points through variance calculation;

calculating movement patterns of each key point in a mouth region using extracted facial key point coordinates, and determining variation degrees of the key points in the mouth region through variance calculation; and configuring calculation results as the dynamic features.

3. An electronic device, comprising:

a memory; and a processor;

wherein the memory is configured to store computer instructions; and the processor is configured to execute the computer instructions to implement the auxiliary diagnosis method of claim 1.

4. A non-transitory computer-readable storage medium, wherein the computer-readable storage medium is configured to store computer instructions; and the computer instructions are configured to be executed by a processor to implement the auxiliary diagnosis method of claim 1.

* * * * *